United States Patent [19]

Chapman et al.

[11] Patent Number: 5,317,041

[45] Date of Patent: May 31, 1994

[54] TICK RELEASE AID

[75] Inventors: Cynthia M. Chapman, P.O. Box 366, Coffeyville, Kans. 67337-0366; Peter M. Lasater, Lenapah, Okla.

[73] Assignee: Cynthia M. Chapman, Lenapah, Okla.

[21] Appl. No.: 957,899

[22] Filed: Oct. 8, 1992

Related U.S. Application Data

[63] Continuation-in-part of Ser. No. 745,554, Aug. 15, 1991, abandoned.

[51] Int. Cl.5 .................. A01N 27/00; A01N 65/00
[52] U.S. Cl. ............................. 514/763; 424/195.1
[58] Field of Search .................. 514/763; 424/195.1

[56] References Cited

U.S. PATENT DOCUMENTS

| | | | |
|---|---|---|---|
| 3,882,248 | 5/1975 | Igimi et al. | 514/763 |
| 4,379,168 | 4/1983 | Dotolo | 514/763 |
| 4,820,739 | 4/1989 | Ramallo et al. | 514/763 |
| 5,010,106 | 4/1991 | Fedin et al. | 514/763 |

Primary Examiner—Allen J. Robinson
Attorney, Agent, or Firm—William S. Dorman

[57] ABSTRACT

A method and composition for effective removal of a tick from a human or animal host.

6 Claims, No Drawings

TICK RELEASE AID

This application is a continuation-in-part of co-pending application Ser. No. 07/745,554, filed Aug. 15, 1991, now abandoned.

BACKGROUND OF THE INVENTION

1. Field of the Invention

The present invention relates to an effective method for removing a tick attached to a human or animal host. More particularly, the present invention relates to a composition which aids in the removal of attached ticks from humans or animals.

2. The Prior Art

Attachment by a tick to a human or animal host can be harmful to the host because the tick is prone to carry a variety of infectious, potentially fatal diseases, such as Rocky Mountain Spotted Fever and Lyme Disease, which can be transmitted from the tick to its host. Prompt and effective removal of an attached tick reduces the chance of disease transmission. For example, a tick carrying Rocky Mountain Spotted Fever disease should be removed from a host within 4 to 6 hours to prevent disease transmission. The recommended method for removal of a tick is to lift a tick out of the host with tweezers by securing the tweezers around the tick, as close to the host's skin as possible, and pulling with a steady, constant motion. However, the recommended method is not always effective in preventing disease transmission because the pulling motion can pull the tick apart, leaving the head, cement and mouth parts in the host.

A general object of the present invention is to provide an effective method for removing a tick from a human or animal host. A more specific object of the present invention is to provide a composition which aids in the removal of a tick from its host. Further objects and advantages of the present invention will be made apparent by the following specification and claims.

SUMMARY OF THE INVENTION

The objects of the present invention can be attained by a composition comprising a citrus peel oil, a carrier fluid suitable for increasing the rate of seepage of the citrus peel oil into human skin or animal hide, and an oil solubilizer suitable for increasing the solubility of the composition in water.

DETAILED DESCRIPTION OF THE PREFERRED EMBODIMENT

1. Composition

The composition of the present invention comprises a citrus peel oil, a carrier fluid, and an oil solubilizer.

The citrus peel oil is a commercial oil expressed from the peel or rind of a citrus fruit, such as an orange, grapefruit, lemon, lime, or tangerine. In one embodiment, the citrus peel oil comprises about 85 volume percent limonene or d-limonene. The citrus peel oil is acidic, and therefore, effective for dissolving the cement which binds the tick to its host. The composition of the present invention comprises from about 25 to about 85 volume percent of citrus peel oil. At least about 25 volume percent citrus peel oil is required to adequately dissolve the cement for effective tick removal. A composition comprising more than about 85 volume percent of citrus peel oil would contain insufficient carrier fluid to increase the seepage rate of the citrus peel oil into human skin or animal hide. To the best of our knowledge, d-limonene is suitable for use in the composition of the present invention in place of the citrus peel oil.

The carrier fluid in the composition of the present invention serves to increase the rate at which the citrus peel oil seeps into the human skin or animal hide where cement bonds the tick to the human or animal. Lower alcohols, such as methyl alcohol, ethyl alcohol, and isopropyl alcohol are suitable carrier fluids for the composition of the present invention. The composition of the present invention comprises at least about 15 volume percent of the isopropyl alcohol to effectively increase the rate of seepage of the citrus peel oil, and no more than about 75 volume percent of the isopropyl alcohol, so that sufficient citrus peel oil for dissolving cement can be present in the composition. One embodiment of the composition of the present invention comprises 25 volume percent of 99 percent grade isopropyl alcohol. Other grades of isopropyl alcohol from about 76 percent and greater, including 91 percent and 95 percent, are suitable carrier fluids for the composition of the present invention.

The composition of the present invention is useful for removing ticks from human or animal hosts. Since the hide of an animal is more sensitive than the skin of a human, the composition of the present invention is preferably diluted for use in removing a tick from an animal host. Water is a readily available, inexpensive diluent. In order to make the composition soluble in water, an oil solubilizer is included in the composition. To our knowledge, any oil solubilizer which increases the solubility of the citrus peel oil/carrier fluid mixture in water is suitable for the composition of the present invention. "TWEEN 80", which comprises polyoxyethylene (20) monooleate, is a suitable oil solubilizer for the composition of the present invention. The composition of the present invention preferably comprises at least about 10 volume percent of the oil solubilizer.

2. Method

The method of the present invention comprises placing about one to two drops of a composition comprising citrus peel oil and a carrier fluid suitable for increasing the seepage rate of the citrus peel oil into human skin or animal hide on and immediately around a tick imbedded into a host and pulling on the tick with tweezers to remove the tick from the host. Best results are obtained when one to two minutes are allowed to pass between placement of the composition on and around the tick and removal of the tick.

3. Examples

The utility and advantages of the method and composition of the present invention are illustrated by the following examples.

Immediately after a two-hour hike in the woods, a woman discovers that a tick imbedded itself in the skin of her neck during the hike. She places two drops of the composition of the present invention comprising about 60 volume percent orange citrus peel oil, about 25 volume percent isopropyl alcohol, and about 15 volume percent of an oil solubilizer comprising polyoxyethylene (20) sorbitan monooleate on the tick and on her skin immediately around the tick. She waits about two minutes to allow the composition to seep into her skin and dissolve the cement which the tick secreted to bond itself to her. She secures the prongs of tweezers around the tick and pulls outwardly. She removes the entire tick, including the head, mouth, and dissolved cement from her body and disposes of it. By removing the entire tick within about two hours of attachment, she has greatly decreased the chance of infection, disease transmission, and itching resulting from the tick imbedding itself in her.

The woman's dog has a tick imbedded in its hide. The woman dilutes the above-described composition at about a one to one ratio and applies it on and around the tick on her dog to aid in removal of the tick from her dog using the above-described method. By diluting the composition, she has decreased the possibility of the composition causing discomfort to her dog.

While the foregoing describes specific preferred embodiments of the present invention, it is to be understood that various modifications and refinements which depart from the described embodiments of the present invention may be adopted without departing from the spirit and scope of the present invention.

What is claimed is:

1. A method in aiding the removal of attached ticks from human and animals hosts comprising:

placing about one to two drops of a composition onto and immediately around a tick imbedded in a host, the composition comprising at least 25 volume percent of a citrus peel oil, at least 15 volume percent of a carrier fluid suitable for increasing the rate at which the citrus peel oil seeps into human skin or animal hide; and at least 10 volume percent an oil solubilizer suitable for increasing solubility of the composition in water; and pulling on the tick with tweezers for removing the tick from the host.

2. A method of claim 1 further comprising waiting one to two minutes between the placement of the composition and removal of the tick.

3. A method of claim 1 wherein the citrus peel oil comprises orange citrus peel oil and the carrier fluid comprises isopropyl alcohol.

4. A method of claim 3 wherein the composition comprises about 60 volume percent orange citrus peel oil, about 25 volume percent isopropyl alcohol, and about volume percent of an oil solubilizer comprising polyoxethylene (20) sorbitan monooleate.

5. A method of claim 4 wherein the host is a human.

6. A method of claim 4 wherein the composition is diluted with water at about a one to one ratio and the host is an animal.

* * * * *